United States Patent [19]

McConnell et al.

[11] 4,145,464
[45] Mar. 20, 1979

[54] ABSORBENT ARTICLES

[75] Inventors: Albert L. McConnell, Wallingford; Richard W. Schutte, Newtown Square, both of Pa.

[73] Assignee: Scott Paper Company, Philadelphia, Pa.

[21] Appl. No.: 732,776

[22] Filed: Oct. 15, 1976

[51] Int. Cl.² ............................. B32B 5/14; B32B 5/16
[52] U.S. Cl. .................................. 428/171; 128/284; 428/283
[58] Field of Search ............... 128/287; 428/280–284, 428/286–291, 296–303, 321, 340, 171, 283, 167, 246, 323, 361, 330, 910, 292; 19/144.5, 145, 145.5; 15/209 R; 427/334, 365, 202; 5/3, 90, 92, 354, 334 R, 354

[56] References Cited

U.S. PATENT DOCUMENTS

| | | | |
|---|---|---|---|
| 2,765,247 | 10/1956 | Graham | 19/145 |
| 3,105,491 | 10/1963 | Harwood | 128/290 R |
| 3,597,306 | 8/1971 | Mesek et al. | 428/283 |
| 3,612,055 | 10/1971 | Mesek et al. | 128/287 |
| 3,856,014 | 12/1974 | Yamauchi | 128/290 R |
| 3,881,490 | 5/1975 | Whitehead et al. | 128/287 |
| 3,903,889 | 9/1975 | Torr | 128/287 |
| 3,908,659 | 9/1975 | Wehrmeyer et al. | 128/287 |
| 3,916,447 | 11/1975 | Thompson | 128/287 |
| 3,934,588 | 1/1976 | Mesek et al. | 128/287 |
| 3,938,522 | 2/1976 | Repke | 128/287 |
| 3,973,067 | 8/1976 | Newman | 428/288 |
| 3,974,319 | 8/1976 | Alibeckoff | 428/283 |

*Primary Examiner*—Robert W. Michell
*Assistant Examiner*—V. Millin
*Attorney, Agent, or Firm*—Martin L. Faigus; William J. Foley

[57] ABSTRACT

A nonwoven absorbent structure usable by itself, as a wiper for example, or usable in combination with other elements, such as an internal absorbent member of a disposable diaper. The absorbent structure includes a dry-formed fibrous section in which the average fiber length is about 1.2 millimeters or longer, and a liquid-transmitting layer of particulate material associated with at least one surface of the fibrous section and having a density greater than that of the fibrous section. At least 50% of the particles, by weight, are of a size that will pass through a 48 mesh screen, and the particulate material is chemically bonded together to form the liquid-transmitting layer(s). Particles of the layer(s) are located between fibers at and adjacent the associated surface(s) of the fibrous section to form a zone in which particles and fibers are intermixed. A disposable diaper in accordance with this invention has an internal absorbent member including a dry-formed fibrous section with the above-described layer of particulate material associated with only one surface thereof. The absorbent member is positioned between a liquid-pervious facing sheet and a backing sheet, and the layer of particulate material is associated with the surface of the fibrous section closest the backing sheet.

6 Claims, 6 Drawing Figures

ABSORBENT ARTICLES

BACKGROUND OF THE INVENTION

1. Field of The Invention

This invention is directed to a nonwoven absorbent structure including a liquid-transmitting layer, and to disposable and limited use articles formed from said structure.

2. Description of the Prior Art

It is well known to employ nonwoven absorbent structures for single or limited use absorbing applications. For example, such structures have been employed as disposable wipers for household and industrial applications, and also as internal absorbent members of disposable diapers. In these types of applications it is highly desirable to provide the nonwoven absorbent structure with a surface region, or layer, for laterally transmitting liquids to aid in achieving effective utilization of the absorbent capacity of said nonwoven structure.

When the absorbent structure is used as a wiper, it is important that it have good wipe dry properties. That is, it is important that the absorbent structure be capable of wiping up and retaining a liquid without leaving an excessive liquid residue behind. When the absorbent structure is employed as an internal member of a disposable diaper, it is important that it be capable of retaining body liquids without becoming flooded in localized areas. When the absorbent structure is employed for the above-referred-to, or similar applications, its performance is improved by enhancing the lateral mobility of liquids along at least one surface thereof.

It is well known to employ a wicking layer in a disposable diaper for the purpose of enhancing the lateral mobility of body liquids to achieve effective utilization of the absorbent components of said diaper. One such wicking layer is disclosed in U.S. Pat. No. 3,763,863, assigned to Johnson and Johnson. The wicking layer disclosed in that patent is a densified, paper-like layer formed insitu on an absorbent batt of loosely compacted fibers by spraying a surface of the batt with moisture, and compressing the batt to densify the moistened surface. This manner of forming the wicking layer is disclosed in detail in U.S. Pat. No. 3,017,304, which is also assigned to Johnson and Johnson.

In forming the wicking layer described in the U.S. Pat. No. 3,017,304 the absorbent batt must include a sufficient weight of fibers to accommodate both the loosely compacted fiber component and the wicking layer component of the batt. Although this wicking layer operates satisfactorily in a disposable diaper, there is always a desire to improve the economics of such diapers. One manner of improving the economics is to form functional components with waste materials. The present invention lends itself to the utilization of waste materials in forming an effective wicking layer.

U.S. Pat. No. 810,115, issued to Green, discloses an absorbent bandage that is primarily intended for surgical purposes. The bandage is of a multilayer construction including a granular layer above a thick mass of absorbent fibers. The granular layer is covered with a facing sheet intended to be placed in engagement with a sore or wound. In this construction the granular layer is positioned for directly receiving body liquids, such as pus or blood, which pass through the facing sheet. Although the granular layer employed in the Green bandage is capable of providing a fluid distributing function, its location adjacent the facing sheet is unsuitable in a disposable diaper construction. Moreover, the layer of granular material disclosed in the Green patent does not cooperate with a dry-formed fibrous section of the type employed in the present invention.

U.S. Pat. Nos. 3,616,180 and 3,816,159, both issued to Newman, relate to nonwoven fiber fleece structures which include fibers in the length range of 50 to 300 microns for the purpose of increasing the opacity of the fleece. The suggestion of including such short fibers in a fiber fleece for the purpose of increasing its opacity does not in any way suggest an arrangement and organization of particulate material in an absorbent fibrous structure for enhancing liquid mobility.

U.S. Pat. No. 3,528,421, issued to Vaillancourt et al, teaches that a layer of hydrous calcium silicate can be employed between upper and lower absorbent layers for the purpose of immobilizing up to 560% of its weight of a liquid which penetrates into that layer. In other words, the function of the layer of hydrous calcium silicate is to immobilize liquids; not to transmit them.

U.S. Pat. No. 3,974,319, issued to Alibeckoff, is referred to herein because it is directed to a web structure which is described as having good wipe dry characteristics. In this construction regenerated cellulose, referred to as "fragments" in the patent, is randomly dispersed throughout the web structure with the greatest concentration being at the web surfaces. The cellulose is applied to the web in the form of a viscose foam, and, in part, produces a reticulated, or cellular-type material. The regenerated cellulose material is not particulate, and does not suggest the inclusion of particulate material in a dry-formed web for the purpose of enhancing liquid mobility.

SUMMARY OF THE INVENTION

A nonwoven absorbent structure in accordance with this invention includes a dry-formed fibrous section in which the average fiber length is about 1.2 millimeters or longer. A liquid-transmitting layer of particulate material is associated with at least one surface of the fibrous section and has a density greater than said section. At least 50% of the particles, by weight, are of a size that will pass through a 48 mesh screen, and the particles are chemically bonded together to form each liquid-transmitting layer. Particles in each layer are located between the fibers at and adjacent an associated surface of the fibrous section to form a zone in which the particles and fibers are intermixed. A portion of the layer of particulate material can extent outwardly beyond the intermixed zone so as to be free of fibers. Alternatively, the entire layer of particulate material can be intermixed with fibers at the surface of the fibrous section. However, in the various embodiments of this invention an interior region of the fibrous section is substantially free of the particles forming the layer(s) to provide a liquid storage region having the capability of retaining a liquid, without laterally wicking the liquid to any significant extent.

In the preferred embodiments of this invention the fibrous sections of the nonwoven structures include as the predominate fiber component, by weight, short cellulosic fibers having an average length in the range of from about 1.2 millimeters to about 6.35 millimeters. When the nonwoven absorbent structure is intended to be employed as a wiper, or for a similar heavy duty application, it is deirable to include a minor proportion (e.g., up to about 25% by weight) of textile-length fibers greater than 6.35 millimeters in length intermingled with the short cellulosic fibers to improve the strength of the nonwoven structure.

Most preferably the liquid-transmitting layer of particulate material has a density greater than 0.12 grams/centimeters$^3$ and a basis weight of from about 30 to about 135 grams/meter$^2$. Applicants have found that a layer of particulate material in the above density and basis weight ranges is highly effective in moving liquids laterally through it to provide for effective utilization of the absorptive area in the fibrous section of the absorbent structure. When the absorbent structure is employed as a wiper, and a layer of particulate material is associated with a surface that is employed to wipe up liquids, the lateral mobility of the liquids through the layer enhances the wipe dry characteristics of the structure. When the fibrous structure is employed as a wiper it is preferable to include a layer of particulate material on each major surface of the absorbent section so that each side of the wiper has good wipe dry characteristics. If desired, two fibrous structures, each including a layer of particulate material on only one surface of a dry-formed fibrous section, can be bonded together to form a wiper in which the particulate layers constitute the outer faces of the composite.

This invention also resides in a disposable diaper having an internal absorbent member which includes an absorbent structure having the above-described layer of particulate material on one surface thereof. In the disposable diaper of this invention a fibrous section of the absorbent structure preferably is formed from 100% short cellulosic fibers having an average length in the range of from about 1.2 millimeters to about 6.35 millimeters (e.g., wood pulp fibers and cotton linters). If desired, the fibrous section can include up to about 25% textile-length fibers greater than 6.35 millimeters to impart strength to the absorbent structure; however, this is generally not necessary.

In the preferred diaper constructions the absorbent structure includes a layer of particulate material associated with only one surface of the fibrous section, and the structure is positioned between a backing sheet and a liquid-previous facing sheet. The layer of particulate material is associated with the surface of the fibrous section which is most remote from the facing sheet. In other words, the wicking layer is most remote from the wearer when the diaper is in use. This wicking layer functions to initially receive urine which passes through the fibrous section of the absorbent structure, and thereafter to wick the urine laterally within the layer for subsequent absorption into dry areas of said fibrous section. When the backing sheet of the diaper is moisture-impervious it acts as a barrier to prevent the urine from passing through the rear of the diaper.

In the preferred embodiments of this invention the particles employed to form the fluid-transmitting layers are short-length cellulosic particles generated in one or more processing steps of the dry-forming operation employed to form the fibrous sections of the absorbent structures. As indicated earlier, the dry-formed fibrous sections in the fibrous structures of this invention preferably include at least a preponderance, by weight, of short cellulosic fibers in the length range of from about 1.2 millimeters to about 6.35 millimeters. In forming these fibrous sections it is common to employ fiberizing equipment to separate the fibers from a feed mat, or lap, and the fiberizing operation generates some short-length particles which are highly suitable for use in forming the fluid-transmitting layers in accordance with this invention. Specifically, in the most preferred embodiment of this invention the fibrous section includes wood pulp fibers which are individualized, or separated from a dense pulp lap sheet in a fiberizing operation. This fiberizing operation generates some short cellulosic particles which are capable of being effectively employed to form the fluid-transmitting layer, as described above. By forming the fluid-transmitting layer from short-length cellulosic particles generated in the dry-forming operation, the fluid-transmitting, or wicking function can be achieved without an incremental increase in fiber cost. This can provide an economic advantage in the construction of single use or limited use absorbent articles, such as disposable diapers and wipers.

It is extremely important to this invention that the particulate material be chemically bonded together to form the liquid-transmitting layers. This chemical bonding is required to immobilize the particulate material against movement so that the integrity of the layer is maintained, and is thereby capable of performing its intended liquid-transmitting function.

When the fibrous structure of this invention is employed as a wiper, or for similar heavy duty applications, it is extremely important that a suitable chemical binder be employed to stablize the particulate material in the layer, or layers, of the fibrous structure. Adhesives which are employed to bond nonwoven structures together are well known in the prior art, and a person skilled in the art can easily chose a suitable adhesive for use in this invention, depending upon the intended application of the wiper. For example, if the wiper is intended to be used in wiping up solvents, the binder which is employed to stablize the layer(s) of particulate material should not be degradable by the solvents. For many industrial and household applications an acrylic latex emulsion, a urethane adhesive or other well-known binder can be employed to bond together the particulate material in the liquid-transmitting layer(s). In accordance with this invention the binder can be employed in a sufficient quantity to stabilize the entire fiber structure so that it can be employed to perform its intended wiping function.

When the fibrous structure of this invention is employed as an internal member of a disposable diaper the particles forming the liquid-transmitting layer do not require the same degree of immobilization as is required when the fibrous structure is employed in wiping applications. More specifically, the fibrous structure in disposable diapers is confined between facing and backing sheets, and these additional components aid in supporting and stablizing the layer of particulate material. However, it is still important that the particulate material be chemically bonded together. In the environment of disposable diapers it has been found suitable to chemically bond the particulate material together with hydrogen bonds. These hydrogen, or hydrate bonds can be established between short cellulosic particles by the application of water to said particles, and thereafter evaporating the water, such as by a drying operation. In addition, starch, dextrin, and similar binders can also be employed to stabilize the layer of particulate material associated with an internal absorbent member of a disposable diaper.

Other objects and advantages of this invention will become apparent by referring to the detailed descrip-

DESCRIPTION OF THE PREFERRED EMBODIMENTS OF THIS INVENTION

Figure 1:
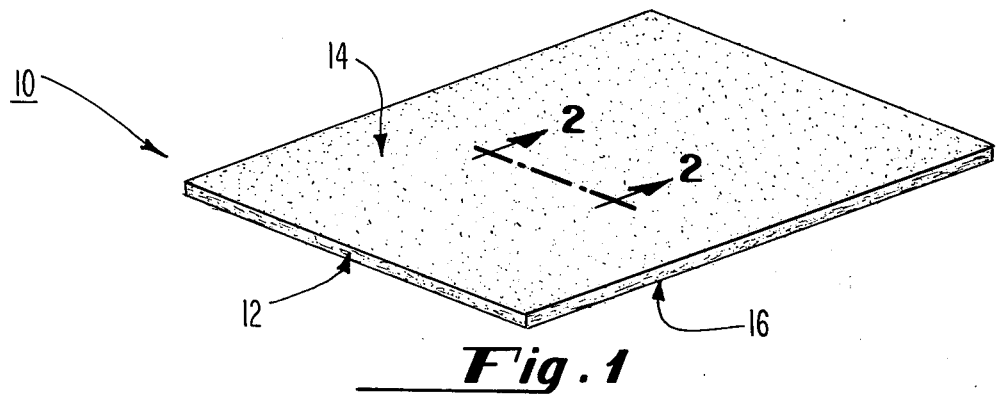
FIG. 1 is an isometric view of a fibrous structure in accordance with this invention.
Figure 2:
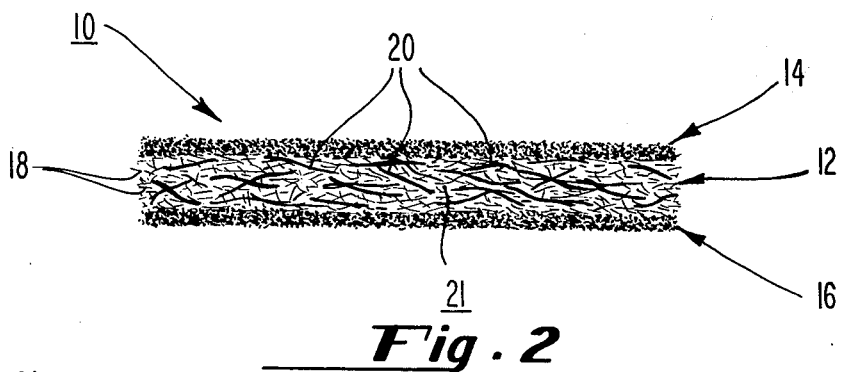
FIG. 2 is a sectional view taken along line 2—2 of FIG. 1 showing, in a somewhat idealized fashion, the construction of the fibrous structure of FIG. 1.

Referring to FIGS. 1 and 2, a nonwoven fibrous structure 10, in the form of a wiper, includes a low density, dry-formed fibrous section 12 and opposed liquid-transmitting layers 14 and 16. The dry-formed fibrous section 12 preferably includes a preponderance, by weight, of short cellulosic fibers 18 in the length range of from between about 1.2 millimeters and about 6.35 millimeters. Most preferably, the short fibers 18 are present in a weight percentage range of from about 75% to about 95%, and the remaining fiber composition includes longer, textile-length fibers 20 for reenforcement. The preferred short cellulosic fiber employed in this invention is wood pulp, since it is readily available, highly absorbent and relatively economical. However, other short cellulosic fibers, such as cotton linters, also can be employed in this invention. The textile-length fibers are 6.35 millimeters or greater, and can include rayon, polyester, and other fibers capable of reenforcing the fibrous section 12. In a preferred construction of this invention the fibrous section 12 has a basis weight in the range of from about 30 to about 200 grams/meter$^2$, and is formed in an air-lay process, such as the one disclosed in U.S. Pat. No. 3,862,472, issued to Norton et al and assigned to Scott Paper Company.

Referring to FIG. 2, the liquid-transmitting layers 14 and 16 are of an identical construction, and are formed from particulate material that is chemically bonded together to stablize the layers. Over 50% of the particulate material, by weight, is of a size that will pass through a 48 mesh screen. This is considerably smaller than the average fiber length of the fibers employed to form the fibrous section 12. The size relationship between the fibers forming the section 12 and the particulate material forming the liquid-transmitting layers 14 and 16 encourages the penetration of particulate material into interstices between the fibers at and adjacent the surfaces of said fibrous section. This provides a zone in which the fibers and particulate material are intermixed, and this zone can either include part, or all of the particulate material forming the liquid-transmitting layer. The intermixed zone of particulate material and fibers provides an unrestricted flow path for liquids between the liquid-transmitting layers 14 and 16, and an internal region 21 of the fibrous section 12. This internal region 21 is substantially free of particles forming the layers 14 and 16, and constitutes a high-volume liquid storage region in which lateral wicking is minimized. A liquid which is wiped by a particulate layer 14 or 16 of the fibrous structure 10 can easily pass into the internal region 21 of the low density fibrous section 12 for retention therein. Preferably, each of the liquid-transmitting layers 14 and 16 has a density greater than 0.12 grams/centimeter$^3$, which is greater than the density of the loosely compacted fibrous section 12. In order to provide a highly favorable capillary structure for the lateral transmission of liquids through the liquid-transmitting layers 14 and 16, each of said layers should have a basis weight of from about 30 to about 135 grams/meter$^2$.

As indicated above, the liquid-transmitting layers 14 and 16 are stablized by chemically bonding the particles therein together. This is extremely important in the constructions of this invention, and is necessary to stablize the particles so that they will not become displaced, and thereby lose their capability of transmitting liquids. Merely mechanically entangling the particulate material with the fibers of the dry-formed section 12 will not adequately immobilize the layer to permit it to perform its liquid-transmitting function when the fibrous structure 10 is in use. In fact, it should be apparent that when the fibrous structure 10 is employed as a wiper, the layers of particulate material must be sufficiently stablized so that they will not fall apart, as they are wiped across a surface. Chemical bonding the particles with an adhesive composition, such as an acrylic latex (e.g., Rohm & Haas HA 8), is preferred for stablizing the particles of the liquid-transmitting layers 14 and 16. The adhesive employed to stablize the layers 14 and 16 has been omitted from the drawings to avoid complicating the illustration of this invention.

In the most preferred embodiments of this invention hydrophilic particulate material is employed to form the liquid-transmitting layers 14 and 16. This enhances the capability of the layers to both retain liquids in its structure, and to laterally move the liquids for absorption into dry areas of the fibrous section 12. Different types of particulate material can be employed to form the layers 14 and 16, such as diatomaceous earth particles, starch particles and, most preferably, short cellulosic particles generated in processing steps of the dry-forming operation employed to form the fibrous section 12. Another suitable material which can be employed as the particulate material is a cellulosic fiber known as Solka-Floc, a trademarked name for fibers supplied by the Brown Company of Berlin, New Hampshire. These latter fibers generally are available in the size range of from about 40 to 110 microns.

For purposes of this application, reference to "particulate material" and "particles", in describing the composition of the liquid-transmitting layers 14 and 16, is intended to include very short fibers, and other fiber-type components within the stated mesh size.

Most preferably, over 50%, by weight, of the particles employed to form the liquid-transmitting layers 14 and 16 are of a size that will pass through a 150 mesh screen. When the particulate material is a fiber component, such as short cellulosic fibers generated in the dry-forming operation, a wet fractionation technique can be employed to determine its mesh size. A suitable wet fractionation technique employed in this invention is the Bauer-McNett technique described in TAPPI Standard T 233 os-75. In accordance with this invention the Bauer-McNett classifier is operated with a series of screens having the following mesh sizes: 14, 28, 48 and 150. In carrying out this test it was found that over 60% of the preferred cellulosic particles, by weight, passed through a 150 mesh screen. When the particulate material is not a fiber-type material it can be classified by well known dry fiber fractionation techniques to determine its mesh size.

In order for the liquid-transmitting layers 14 and 16 to perform their intended fluid-spreading function the capillary structure within each layer should be smaller than the capillary structure of the dry-formed fibrous section 12. To achieve this construction over 50%, by weight, of the short cellulosic fibers employed in the formation of the fibrous section 12 is of a larger mesh size than over 50%, by weight, of the particulate material employed to form the liquid-transmitting layers 14 and 16. For example, in a preferred construction of this invention the short cellulosic fibers 18 employed in forming the fibrous section 12 have an average fiber length, by weight, of 2.4 millimeters. Over 50%, by weight, of those fibers were in a size range greater than 14 mesh. In other words, over 50% of the fibers were retained on a 14 mesh screen of the Bauer-McNett classifier. However, in the preferred construction of the fibrous structure 10 the particles forming the liquid-transmitting layers 14 and 16 are cellulosic particles generated in the dry forming operation employed to form the fibrous section 12, and only 0.3% of these particles are retained on the 14 mesh screen. In fact, approximately 62% of these cellulosic particles passed through a 150 mesh screen.

In FIG. 2, the liquid-transmitting layers 14 and 16 are shown as being continuously distributed over each of the opposed surfaces of the fibrous section 12. However, it is within the scope of this invention to include a liquid-transmitting layer on only one of the major surfaces of the fibrous section 12. This latter construction is suitable for use in a wiper having two-sided properties. That is, as a wiper in which the opposed surfaces are intended to perform different wiping functions. It is also within the scope of this invention to include a discontinuous liquid-transmitting layer over one or both surfaces of a fibrous section.

Figure 3:
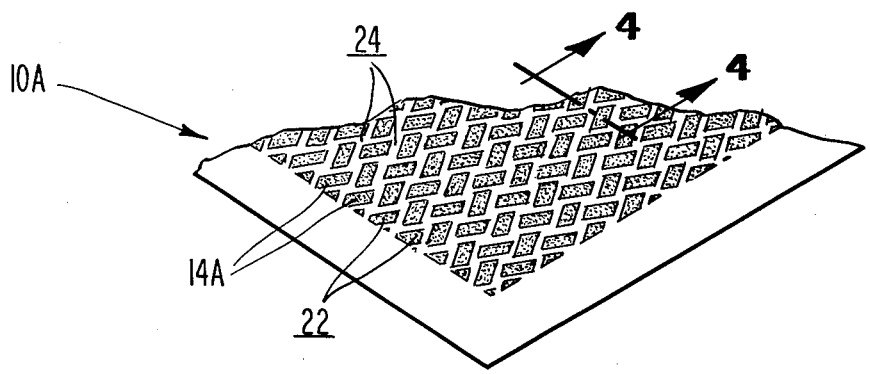
FIG. 3 is a fragmentary isometric view of a second embodiment of a fibrous structure in accordance with this invention.
Figure 4:
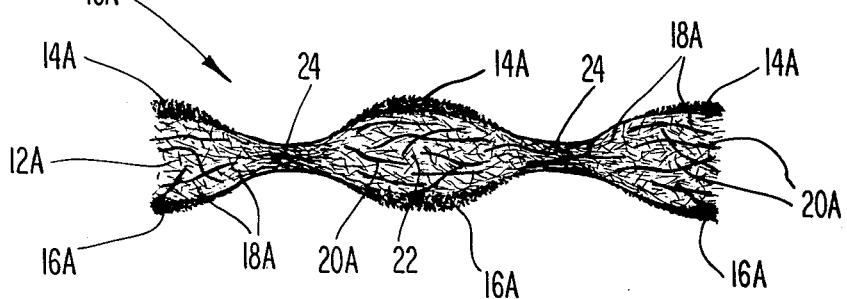
FIG. 4 is a sectional view along line 4—4 of FIG. 3 showing, in a somewhat idealized fashion, the construction of the fibrous structure of FIG. 3.

An embodiment of a wiper including discontinuous liquid-transmitting layers is shown in FIGS. 3 and 4, and is designated by the numeral 10A. This wiper is shown as including an embossed, dry-formed fibrous section 12A similar to the air-laid web disclosed in copending application Ser. No. 497,024, filed Aug. 13, 1974, and assigned to Scott Paper Company. That application is hereby incorporated by reference. The basis weight range of the wiper 10A can be varied from between about 30 to about 200 grams/meters$^2$.

The embossed fibrous section 12A includes high loft, low-density regions 22, and compressed, higher-density regions 24. The liquid-transmitting layer on each side of the fibrous section 12A is shown as being in discrete, spaced-apart sections associated only with the surfaces of the high loft regions 22. These discrete sections are designated 14A on one side of the wiper 10A, and 16A on the opposite side of said wiper. These sections 14A and 16A are associated with the opposed surfaces of the high loft, low-density regions 22 for the purpose of providing a capillary structure that enhances the liquid-transmitting properties of the wiper 10A in those regions. It is desirable to provide such a capillary structure at the outer surfaces of the high loft regions 22, since those surfaces generally are the ones that come into most intimate contact with liquids to be wiped up. The higher density, compressed regions 24 have a capillary structure which is quite favorable to the transmission of liquids. Accordingly, it is not necessary to include liquid-transmitting sections at the surfaces of the wiper 10A in the compressed regions 24. However, if desired, the liquid-transmitting layers can be formed continuously over the opposed surfaces of the wiper 10A to thereby be associated with the wiper surfaces in the compressed regions 24, as well as with the wiper surfaces in the high loft regions 22. The chemical bonding material employed to bond the particles together in the liquid-transmitting sections 14A and 16A can also be employed to bond the fibrous section 12A to complete the formation of a self-sustaining wiper structure.

It should be understood that the liquid-transmitting sections 14A and 16A are of the same particulate construction, and can be varied within the same parameters, as the earlier-described liquid-transmitting layers 14 and 16. Also, the fibrous section 12A preferably includes a preponderance, by weight, of short cellulosic fibers 18A under about 6 millimeters in length, and a minor proportion, by weight, of longer textile-length fibers 20A for reenforcing the section 12. The particular fiber construction of the section 12A can be identical to that of the fibrous section 12 described earlier in connection with FIGS. 1 and 2.

The wipe dry capability of a nonwoven web for liquids is tested by the following procedure:

first, a sample of the web being tested is mounted on a padded surface of a sled (10 cm × 6.3 cm);

second, the sled is mounted on an arm designed to traverse the sled across a rotating disc;

third, the sled is weighted so that the combined weight of the sled and sample is about 763 grams;

fourth, the sled and traverse arm are positioned on a horizontal rotatable disc with the sample being pressed against the surface of the disc by the weighted sled (the sled and traverse arm being positioned with the leading edge of the sled (6.3 cm side) just off the center of the disc and with the 10 cm centerline of the sled being positioned along a radial line of the disc so that the trailing 6.3 cm edge is positioned near the perimeter of the disc);

fifth, 0.5 milliliters of water is placed on the center of the disc in front of the leading edge of the sled (sufficient surfactant is added to the water so that it leaves a film, rather than discrete droplets, when wiped). For this test a 0.1% Tergitol 15-S-15 solution (Union Carbide) was used;

sixth, the disc having a diameter of about 60 centimeters, is rotated at about 65 rpm while the traverse arm moves the sled across the disc at a speed of about 2½ centimeters per second until the trailing edge of the sled crosses off the outer edge of the disc at which point the test is stopped (about 15 seconds from start to finish of the test);

seventh, the wiping effect of the test sample upon the water solution is observed during the test as the sled wipes across the disc, in particular the wetted surface is observed and a wiped dry area appears at the center of the disc and enlarges radially on the disc;

eighth, at the moment the test is stopped (when the trailing edge of the sled passes off the edge of the disc) the size of the wiped dry area in square centimeters at the center of the disc is observed (if any).

The test is performed under constant temperature and relative humidity conditions (70° F. ± 2° F., 65% relative humidity ± 2%). The test is repeated and the average of the wiped dry area observation (step 8) in square centimeters is defined as the wipe dry index for the sample being tested. To aid in the observation of the size of the area on the disc wiped dry by the test sample (steps 7 and 8), concentric circular score lines are made on the surface of the disc corresponding to the 50, 100, 200, 300, 400 500 and 750 square centimeter circles so that the size of the dry area can be quickly determined by visually comparing the dry area to a reference score line of known area.

It has been found that a dry-formed fibrous section including a layer of particulate material in the preferred density range of greater than 0.12 grams/centimeter$^3$ and in the preferred basis weight range of about 30 to 135 grams/meter$^2$ enhances the wipe dry characteristics of the composite approximately ten-fold, as compared to the wipe-dry characteristics of the fibrous section by itself.

Figure 5:
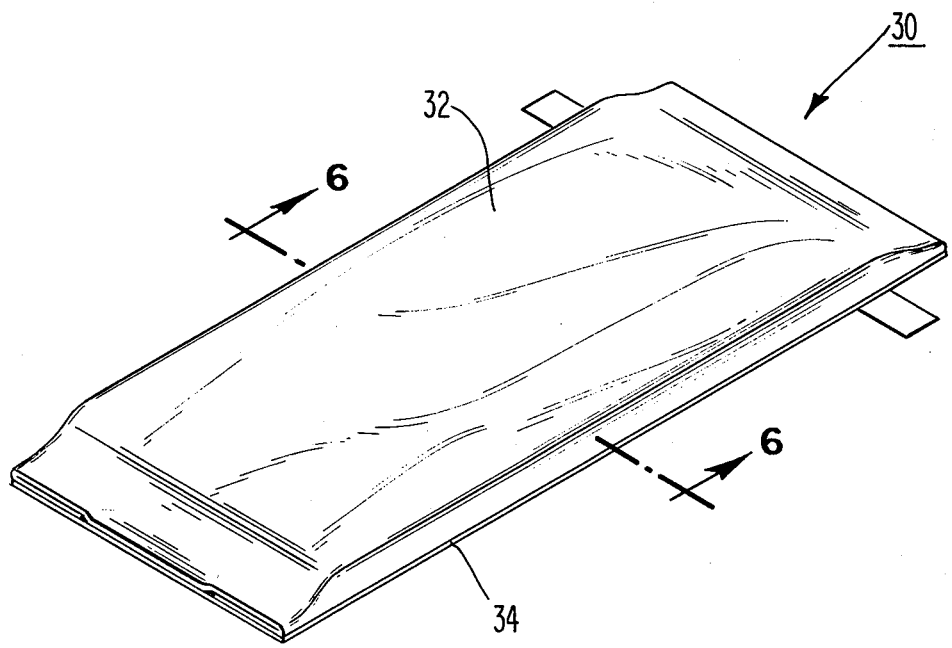
FIG. 5 is an isometric view of a disposable diaper in accordance with this invention.
Figure 6:
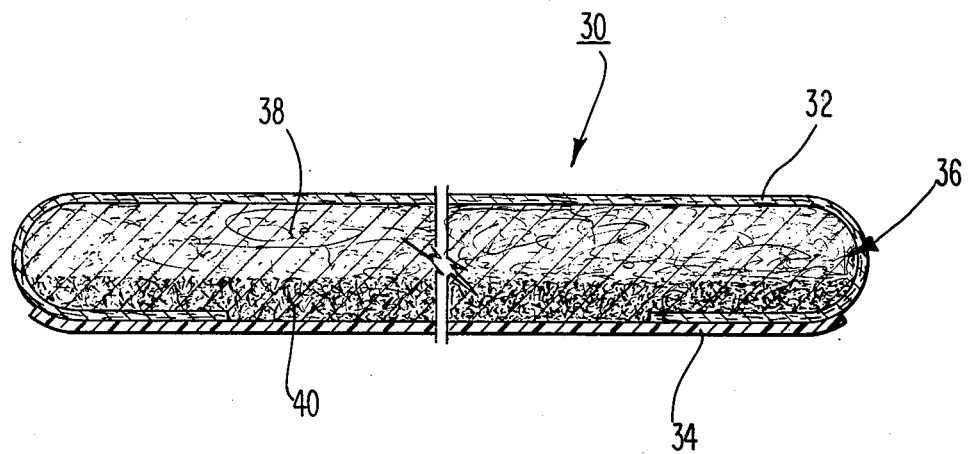
FIG. 6 is a sectional view taken along line 6—6 of FIG. 5 showing, in a somewhat idealized fashion, the construction of the nonwoven absorbent structure employed in the disposable diaper.

Referring now to FIGS. 5 and 6, a representative disposable diaper 30 in accordance with this invention has a moisture-pervious facing sheet 32, a moisture-impervious backing sheet 34 and an internal core including an absorbent member 36. The construction of the disposable diaper 30 can be varied within wide limits. However, it is important that the absorbent member 36 include, as at least one component thereof, a dry-formed absorbent fibrous section, or batt 38 formed predominately of short cellulosic fibers having an average length of from about 1.2 millimeters to about 6.35 millimeters. Wood pulp fibers are within the above-stated fiber length range and are conventionally employed to form such a batt.

In accordance with this invention the absorbent member 36 includes a liquid-transmitting layer 40 formed from particulate material which is chemically bonded together to form a continuum for receiving body fluids that pass through the fibrous batt 38, and thereafter, wicking the body fluids laterally for subsequent absorption into dry areas of said batt. The wicking layer 40 is formed in engagement with the surface of the fibrous batt 38 which is most remote from the moisture-impervious facing sheet 32.

The particulate material employed to form the wicking layer 40 is identical to the particulate material that can be employed to form the various liquid-transmitting layers described earlier. Specifically, over 50% of the particulate material, by weight, is of a size that will pass through a 48 mesh screen. Most preferably, over 50% of the particulate material will pass through a 150 mesh screen. Most preferably the particulate material is cellulosic particles generated in the dry-forming operation employed to form the fibrous batt 18. Most preferably the wicking layer 40 is continuous over the lower surface of the batt 38, and has a density greater than 0.12 grams/centimeter$^3$. This is greater than the density of the loosely compacted fibrous batt 38, which preferably has a density below 0.10 grams/centimeter$^3$. Also, in order to provide a highly favorably capillary structure for wickability, the wicking layer 40 preferably has a basis weight of from about 30 to about 135 grams/meters$^2$.

The most significant difference between the liquid-transmitting layers described earlier in connection with wipers 10 and 10A, and the wicking layer 40 employed in the disposable diaper 30, is the nature of the chemical bonding material which can be employed to bond the particles together. Specifically, the absorbent member 36, which includes the wicking layer 40, is confined between the facing sheet 32 and the backing sheet 34. This tends to provide some confinement for the wicking layer 40. Moreover, the wicking layer 40 is not required to be rubbed against a surface for the purpose of picking up liquids, as is the case in using wipers. Therefore, the chemical bonding of the particles in the wicking layer 40 is not required to be as tenacious as the chemical bonding of the particles in the liquid-transmitting layers of the wipers 10 and 10A. In accordance with the diaper variant of this invention the chemical bonding of the particulate material in the wicking layer can be achieved by forming hydrogen bonds between the particles. When the particles are cellulosic, the hydrogen bonds can be formed by applying water to those particles. Alternatively, hydrogen bonds can be formed between particles by employing hydrated starch, or similar material as the bonding agent. Although it is not necessary to employ more tenacious chemical binders, such as wet strength resins or acrylic latices, to bond the particles together in a diaper wicking layer, it is within the scope of this invention to do so.

In order for the wicking layer 40 to perform its intended fluid-spreading function relative to the fibrous batt 38, its capillary structure should be smaller than the capillary structure of said batt. This relationship between the capillary structures has been discussed in detail in connection with the nonwoven fibrous structures shown in FIGS. 1–4, and will not be repeated herein. Suffice it to state that over 50%, by weight, of the short cellulosic fibers employed to form the absorbent batt 38 is of a larger mesh size than over 50%, by weight, of the particulate material employed to form the wicking layer 40. The length and mesh size of the short cellulosic fibers employed to form the batt 38, as well as the mesh size of the preferred particulate material employed to form the wicking layer 40 are identical to that described in connection with the fibrous structures disclosed in FIGS. 1–4. Therefore, that discussion will not be repeated herein.

Having described our invention we claim:

1. An absorbent structure including a dry-formed fibrous section including a preponderance, by weight, of short cellulosic fibers that are in the length range of from between about 1.2 millimeters and about 6.35 millimeters and that are of a size that would be retained on a 14 mesh screen, said fibrous section including opposed major surfaces and being embossed to provide a plurality of low density, high loft regions and high-density, compressed regions disposed over substantially the entire extent of the fibrous section, a liquid-transmitting layer formed of particucate material that maintains its particulate form when contacted with liquids and that is added to both major surfaces of the fibrous section, said particulate material being chemically bonded together and at least 50% of the particles in each layer, by weight, being of a size that will pass through a 48 mesh screen, said layers of particulate material having a density greater than that of the fibrous section and the particulate material in the layers being located between fibers at and adjacent the associated surfaces of the fibrous section to form a zone in which particulate material and fibers are intermixed, said particulate layers being adapted to wick liquids laterally for subsequent absorption into dry regions of the fibrous section and said fibrous section including an internal region that is substantially free of particles forming the liquid transmitting layers.

2. The absorbent structure according to claim 1, wherein over 50% of the particulate material, by weight, is of a size that will pass through a 150 mesh screen.

3. The absorbent structure according to claim 1, including an adhesive means for chemically bonding together the particulate material in the liquid-transmitting layers.

4. The absorbent structure according to claim 1, wherein the liquid-transmitting layers are in spaced-apart sections associated only with low-density, high-loft surface regions of said fibrous section.

5. The absorbent structure according to claim 1, wherein said fibrous section includes a minor proportion, by weight, of textile-length fibers greater than 6 millimeters in length for enhancing the structural integrity of said section.

6. The absorbent structure according to claim 1, wherein the short cellulosic fibers of the absorbent fibrous section are wood pulp fibers, and the particulate material of the liquid-transmitting layers include wood pulp material.

* * * * *